Figure 1A:
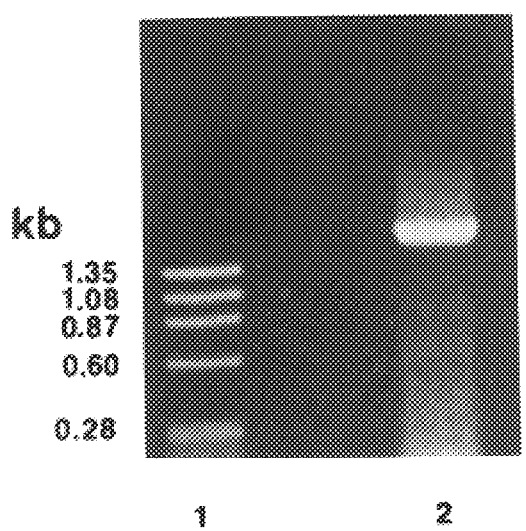

US005846771A

United States Patent [19]
Kron et al.

[11] Patent Number: 5,846,771
[45] Date of Patent: Dec. 8, 1998

[54] **ASSAY FOR DETECTION OF FILARIASIS USING RECOMBINANT ASPARAGINYL-TRNA SYNTHETASE FROM THE HUMAN FILRIAL PARASITE, *BRUGIA MALAYI***

[75] Inventors: Michael A. Kron, Okemos, Mich.; Reuben Leberman, Claix, France

[73] Assignees: Board of Trustees operating Michigan State University, East Lansing, Mich.; European Molecular Biology Laboratory, Heidelberg, Germany

[21] Appl. No.: 802,991

[22] Filed: Feb. 21, 1997

Related U.S. Application Data

[62] Division of Ser. No. 628,103, Apr. 9, 1996, Pat. No. 5,695,962, which is a division of Ser. No. 441,534, May 15, 1995, Pat. No. 5,561,054.

[51] Int. Cl.$^6$ ........................................................ C12P 21/06
[52] U.S. Cl. ............................................. 435/69.1; 435/7.4
[58] Field of Search ..................................... 435/69.1, 7.4

[56] References Cited

U.S. PATENT DOCUMENTS 5,561,054  10/1996  Kron et al. ............................ 435/69.1

OTHER PUBLICATIONS

Chandrashekar, R., et al., Mol. Biochem. Parasitology, vol. 64(2), 261–271 (Apr. 1994).
Dissanayake, S., et al., Am. J. Trop. Med. Hyg. 50(6), 727–734 (Jun. 1994).
Dissanayake, S., et al., Molecular and Biochemical Parasitology 56, 259–268 (1992).
Dissanayake, S., et al., Molecular and Biochemical Parasitology 56, 269–278 (1992).
Philipp, M., et al., Ann Rev. Microbiol. 42 685–716 (1988).
Carter, T. W., Ann. Rev. Biochem. 62 715–748 (1993).
EMBL Annual Report, 239–240 (1994).
Eriani, G., et al., Nature 347 203–206 (1990).
Cusack, S., et al., Nature 347 249–255 (1990).
Nilson, T. W., et al., Proc. Natl. Acad. Sci. USA 85 3604–3607 (1988).
Kron, M., et al., Mol. Biochem. Parasit. 52 289–292 (1992).
Cusack, S., et al., Nucleic Acids Research 19 3489–3497 (1991).
Targoff, I., et al., J. Clin. Invest. 91 2556–2564 (1993).
Love, L. A., et al., Medicine 70 360–374 (1991).
Bunn, C. C., et al., J. Exp. Med. 163 1281–1291 (1986).
Anselme, J., et al., Gene 84 481–485 (1989).
Bolle, P–A., et al., Yeast 8 205–213 (1992).
Bochner, B.R., et al., Cell, 37 225–232 (1984).
Segal, E., et al., Exp. Cell. Res. 167 119–126 (1986).
Walter, R.D., Trop. Med. Parasitol. 37 95 (1986).
Biou, V., et al., Science 263 1404–1410 (1994).
Belrhali, H., et al., Science 263 1432–1436 (1994).
Cusack, S. et al, Nucleic Acid Research, vol. 19(13), pp. 3489–3498, 1991.
Kron, M. et al, FEBs Letters, vol. 374, pp. 122–124, 1995.
Nilsen, T. W. et al, Proc. Nat'l Acad Sci, USA vol. 85, pp. 3604–3607, May, 1988.

*Primary Examiner*—James C. Housel
*Assistant Examiner*—Ginny Allen Portner
*Attorney, Agent, or Firm*—Ian C. McLeod

[57] ABSTRACT

Recombinant asparaginyl tRNA synthetase from human filarial parasite *Brugia malayi*. The enzyme is used in an assay for inhibitors of the synthetase and can be used as an antigen for producing antibody inhibitors of the disease, either monoclonal or polyclonal. The antibodies can be used to detect the synthetase and related enzymes. In particular, the synthetase can be used to produce an antibody to be used for detecting filarial nematodes. The synthetase can be used to produce adenylated nucleosides.

2 Claims, 4 Drawing Sheets

```
Motif 1 antBM    M R E H F Y N A G Y V E V A P P T L
antOV    M R E H F Y N A G Y V E V A P P T L
NRSSC    F M L Y F Q K N H F T K V S P P I L
NRSEC    L H R F F N E Q G F F W V S T P L I Motif 2 antBM    L G D V F H L H C S Y R A E K S R T R R H L A E Y A H V E A E C P F I T
antOV    D A Q Y H I Y F E L F R A E K S R T R R H L A E Y A H V E A E C P F I T
NRSSC    L S R C W T L S P C F R A E K S D T P R H L S E F W M L E V E M C F V N
NRSEC    L S K I Y T F G P T F R A E N S N T S R H L A E F W M L E P E V A F A N Motif 3 antBM    Y G T C P H G G Y G L G L E R F I C W L T N T N H I R D V C L Y P R
antOV    M E P V P H G G Y G L G L E R Y L - F L T N T N H
NRSSC    E G S A P H G G F G L G F E R F I S Y L Y G N H N I K D A I P F Y R
NRSEC    Y G T V P H S G F G L G F E R L I A Y V T G V Q N V R D V I P F P R
```

Motif 1

```
antBM   M R E H F Y N A G Y V E V A P P T L
antOV   M R E H F Y N A G Y V E V A P P T L
NRSSC   F M L Y F Q K N H F T K V S P P I L
NRSEC   L H R F F N E Q G F F W V S T P L I
```

Motif 2

```
antBM   L G D V F H L H C S Y R A E K S R T R R H L A E Y A H V E A E C P F I T
antOV   D A Q Y H I Y F E L F R A E K S R T R R H L A E Y A H V E A E C P F I T
NRSSC   L S R C W T L S P C F R A E K S D T P R H L S E F W M L E V E M C F V N
NRSEC   L S K I Y T F G P T F R A E N S N T S R H L A E F W M L E P E V A F A N
```

Motif 3

```
antBM   Y G T C P H G G Y G L G L E R F I C W L T N T N H I R D V C L Y P R
antOV   M E P V P H G G Y G L G L E R Y L - F L T N T N H         R
NRSSC   E G S A P H G G F G L G L E R F I S Y L Y G N H N I K D A I P F Y R
NRSEC   Y G T V P H S G F G L G L E R L I A Y V T G V Q N V R D V I P F P R
```

FIG.3

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 33 Base Pairs ( B ) TYPE: Nucleic Acid
( C ) STRANDEDNESS: Single
( D ) TOPOLOGY: Linear ( i i ) MOLECULE TYPE:
( A ) DESCRIPTION: Synthetic DNA ( i i i ) HYPOTHETICAL: No ( i v ) ANTI-SENSE: No ( v i ) ORIGINAL SOURCE:
( A ) ORGANISM: Brugia malayi ( v i i ) IMMEDIATE SOURCE:
( A ) LIBRARY:

( x i ) SEQUENCE DESCRIPTION: SEQ ID NO: 1:

ATGACTGTTT ATATTTGTCC AGAAACTGGA GAT  33

( 2 ) INFORMATION FOR SEQ ID NO:2:

( i ) SEQUENCE CHARACTERISTICS:
( A ) LENGTH: 38 Base Pairs
( B ) TYPE: Nucleic Acid
( C ) STRANDEDNESS: Single
( D ) TOPOLOGY: Linear ( i i ) MOLECULE TYPE:
( A ) DESCRIPTION: Synthetic DNA ( i i i ) HYPOTHETICAL: No ( i v ) ANTI-SENSE: No ( v i ) ORIGINAL SOURCE:
( A ) ORGANISM: Brugia malayi ( v i i ) IMMEDIATE SOURCE:
( A ) LIBRARY:

( x i ) SEQUENCE DESCRIPTION: SEQ ID NO: 2:

TTGAATTCTT ATGGGACACA TCGACCAACA AAGCGAGG  38

( 2 ) INFORMATION FOR SEQ ID NO:3:

( i ) SEQUENCE CHARACTERISTICS:
( A ) LENGTH: 18 Amino Acids
( B ) TYPE: Amino Acid
( C ) STRANDEDNESS: Single
( D ) TOPOLOGY: Linear ( i i ) MOLECULE TYPE:
( A ) DESCRIPTION: Motif of synthetase ( i i i ) HYPOTHETICAL: No ( i v ) ANTI-SENSE: No ( v i ) ORIGINAL SOURCE:
( A ) ORGANISM: Brugia malayi ( v i i ) IMMEDIATE SOURCE:
( A ) LIBRARY:

( x i ) SEQUENCE DESCRIPTION: SEQ ID NO: 3:

Met Arg Glu His Phe Tyr Asn Ala Gly Tyr Val Glu Val Ala Pro Pro Thr Leu
             5                   10                  15

( 2 ) INFORMATION FOR SEQ ID NO:4:

( i ) SEQUENCE CHARACTERISTICS:
( A ) LENGTH: 18 Amino Acids
( B ) TYPE: Amino Acid (C) STRANDEDNESS: Single
(D) TOPOLOGY: Linear (ii) MOLECULE TYPE:
(A) DESCRIPTION: Motif of synthetase (iii) HYPOTHETICAL: No (iv) ANTI-SENSE: No (vi) ORIGINAL SOURCE:
(A) ORGANISM: Onchocerca volvulus (vii) IMMEDIATE SOURCE:
(A) LIBRARY:

(xi) SEQUENCE DESCRIPTION: SEQ ID NO: 4:

Met Arg Glu His Phe Tyr Asn Ala Gly Tyr Val Glu Val Ala Pro Pro Thr Leu
              5                   10                  15

(2) INFORMATION FOR SEQ ID NO:5:

(i) SEQUENCE CHARACTERISTICS:
(A) LENGTH: 18 Amino Acids
(B) TYPE: Amino Acid
(C) STRANDEDNESS: Single
(D) TOPOLOGY: Linear (ii) MOLECULE TYPE:
(A) DESCRIPTION: Motif of Synthetase (iii) HYPOTHETICAL: No (iv) ANTI-SENSE: No (vi) ORIGINAL SOURCE:
(A) ORGANISM: Escherichia coli (vii) IMMEDIATE SOURCE:
(A) LIBRARY:

(xi) SEQUENCE DESCRIPTION: SEQ ID NO: 5:

Phe Met Leu Tyr Phe Gln Lys Asn His Phe Thr Lys Val Ser Pro Pro Ile Leu
              5                   10                  15

(2) INFORMATION FOR SEQ ID NO:6:

(i) SEQUENCE CHARACTERISTICS:
(A) LENGTH: 18 Amino Acids
(B) TYPE: Amino Acid
(C) STRANDEDNESS: Single
(D) TOPOLOGY: Linear (ii) MOLECULE TYPE:
(A) DESCRIPTION: Motif of Synthetase (iii) HYPOTHETICAL: No (iv) ANTI-SENSE: No (vi) ORIGINAL SOURCE:
(A) ORGANISM: Saccharomyces cerevisiae (vii) IMMEDIATE SOURCE:
(A) LIBRARY:

(xi) SEQUENCE DESCRIPTION: SEQ ID NO: 6:

Leu His Arg Phe Phe Asn Glu Gln Gly Phe Phe Trp Val Ser Thr Pro Leu Ile
              5                   10                  15

(2) INFORMATION FOR SEQ ID NO:7:

(i) SEQUENCE CHARACTERISTICS:
(A) LENGTH: 36 Amino Acids ( B ) TYPE: Amino Acid
                ( C ) STRANDEDNESS: Single
                ( D ) TOPOLOGY: Linear ( i i ) MOLECULE TYPE:
                ( A ) DESCRIPTION: Motif of Synthetase ( i i i ) HYPOTHETICAL: No ( i v ) ANTI-SENSE: No ( v i ) ORIGINAL SOURCE:
                ( A ) ORGANISM: Brugia malayi ( v i i ) IMMEDIATE SOURCE:
                ( A ) LIBRARY:

( x i ) SEQUENCE DESCRIPTION: SEQ ID NO: 7:

Leu Gly Asp Val Phe His Leu His Cys Ser Tyr Arg Ala Glu Lys Ser Arg Thr
                    5                   10                  15

Arg Arg His Leu Ala Glu Tyr Ala His Val Glu Ala Glu Cys Pro Phe Ile Thr
    20                  25                  30                  35

( 2 ) INFORMATION FOR SEQ ID NO:8:

( i ) SEQUENCE CHARACTERISTICS:
                ( A ) LENGTH: 36 Amino Acids
                ( B ) TYPE: Amino Acid
                ( C ) STRANDEDNESS: Single
                ( D ) TOPOLOGY: Linear ( i i ) MOLECULE TYPE:
                ( A ) DESCRIPTION: Motif of Synthetase ( i i i ) HYPOTHETICAL: No ( i v ) ANTI-SENSE: No ( v i ) ORIGINAL SOURCE:
                ( A ) ORGANISM: Onchocerca volvulus ( v i i ) IMMEDIATE SOURCE:
                ( A ) LIBRARY:

( x i ) SEQUENCE DESCRIPTION: SEQ ID NO: 8:

Asp Ala Gln Tyr His Ile Tyr Phe Glu Leu Phe Arg Ala Glu Lys Ser Arg Thr
                    5                   10                  15

Arg Arg His Leu Ala Glu Tyr Ala His Val Glu Ala Glu Cys Pro Phe Ile Thr
    20                  25                  30                  35

( 2 ) INFORMATION FOR SEQ ID NO:9:

( i ) SEQUENCE CHARACTERISTICS:
                ( A ) LENGTH: 36 Amino Acids
                ( B ) TYPE: Amino Acid
                ( C ) STRANDEDNESS: Single
                ( D ) TOPOLOGY: Linear ( i i ) MOLECULE TYPE:
                ( A ) DESCRIPTION: Motif of Synthetase ( i i i ) HYPOTHETICAL: No ( i v ) ANTI-SENSE: No ( v i ) ORIGINAL SOURCE:
                ( A ) ORGANISM: Escherichia coli ( v i i ) IMMEDIATE SOURCE:
                ( A ) LIBRARY:

( x i ) SEQUENCE DESCRIPTION: SEQ ID NO: 9:

Leu Ser Arg Cys Trp Thr Leu Ser Pro Cys Phe Arg Ala Glu Lys Ser Asp Thr

```
                              5                             10                            15
Pro  Arg  His  Leu  Ser  Glu  Phe  Trp  Met  Leu  Glu  Val  Glu  Met  Cys  Phe  Val  Asn
     20                       25                      30                            35
```

( 2 ) INFORMATION FOR SEQ ID NO:10:

( i ) SEQUENCE CHARACTERISTICS:
        ( A ) LENGTH: 36 Amino Acids
        ( B ) TYPE: Amino Acid
        ( C ) STRANDEDNESS: Single
        ( D ) TOPOLOGY: Linear ( i i ) MOLECULE TYPE:
        ( A ) DESCRIPTION: Motif of Synthetase ( i i i ) HYPOTHETICAL: No ( i v ) ANTI-SENSE: No ( v i ) ORIGINAL SOURCE:
        ( A ) ORGANISM: Saccharomyces cerevisiae ( v i i ) IMMEDIATE SOURCE:
        ( A ) LIBRARY:

( x i ) SEQUENCE DESCRIPTION: SEQ ID NO: 10:

```
Leu  Ser  Lys  Ile  Tyr  Thr  Phe  Gly  Pro  Thr  Phe  Arg  Ala  Glu  Asn  Ser  Asn  Thr
               5                       10                      15
Ser  Arg  His  Leu  Ala  Glu  Phe  Trp  Met  Leu  Glu  Pro  Glu  Val  Ala  Phe  Ala  Asn
     20                       25                      30                            35
```

( 2 ) INFORMATION FOR SEQ ID NO:11:

( i ) SEQUENCE CHARACTERISTICS:
        ( A ) LENGTH: 34
        ( B ) TYPE: Amino Acids
        ( C ) STRANDEDNESS: Single
        ( D ) TOPOLOGY: Linear ( i i ) MOLECULE TYPE:
        ( A ) DESCRIPTION: Motif of Synthetase ( i i i ) HYPOTHETICAL: No ( i v ) ANTI-SENSE: No ( v i ) ORIGINAL SOURCE:
        ( A ) ORGANISM: Brugia malayi ( v i i ) IMMEDIATE SOURCE:
        ( A ) LIBRARY:

( x i ) SEQUENCE DESCRIPTION: SEQ ID NO: 11:

```
Tyr  Gly  Thr  Cys  Pro  His  Gly  Gly  Tyr  Gly  Leu  Gly  Leu  Glu  Arg  Phe  Ile  Cys
               5                       10                      15
Trp  Leu  Tyr  Asn  Thr  Asn  His  Ile  Arg  Asp  Val  Cys  Leu  Tyr  Pro  Arg
     20                       25                      30
```

( 2 ) INFORMATION FOR SEQ ID NO:12:

( i ) SEQUENCE CHARACTERISTICS:
        ( A ) LENGTH: 25 Amino Acids
        ( B ) TYPE: Amino Acid
        ( C ) STRANDEDNESS: Single
        ( D ) TOPOLOGY: Linear ( i i ) MOLECULE TYPE:
        ( A ) DESCRIPTION: Motif of Synthetase ( i i i ) HYPOTHETICAL: No ( i v ) ANTI-SENSE: No (vi) ORIGINAL SOURCE:
    (A) ORGANISM: Onchocerca volvulus (vii) IMMEDIATE SOURCE:
    (A) LIBRARY:

(xi) SEQUENCE DESCRIPTION: SEQ ID NO: 12:

Met Glu Pro Val Pro His Gly Gly Tyr Gly Leu Gly Leu Glu Arg Tyr Leu Xaa
              5                   10                  15

Phe Leu Thr Asn Thr Asn His
        20              25

(2) INFORMATION FOR SEQ ID NO:13:

(i) SEQUENCE CHARACTERISTICS:
        (A) LENGTH: 34 Amino Acids
        (B) TYPE: Amino Acid
        (C) STRANDEDNESS: Single
        (D) TOPOLOGY: Linear (ii) MOLECULE TYPE:
        (A) DESCRIPTION: Motif of Synthetase (iii) HYPOTHETICAL: No (iv) ANTI-SENSE: No (vi) ORIGINAL SOURCE:
        (A) ORGANISM: Escherichia coli (vii) IMMEDIATE SOURCE:
        (A) LIBRARY:

(xi) SEQUENCE DESCRIPTION: SEQ ID NO: 13:

Glu Gly Ser Ala Pro His Gly Gly Phe Gly Leu Gly Phe Glu Arg Phe Ile Ser
              5                   10                  15

Tyr Leu Tyr Gly Asn His Asn Ile Lys Asp Ala Ile Pro Phe Tyr Arg
        20              25              30

(2) INFORMATION FOR SEQ ID NO:14:

(i) SEQUENCE CHARACTERISTICS:
        (A) LENGTH: 34 Amino Acids
        (B) TYPE: Amino Acid
        (C) STRANDEDNESS: Single
        (D) TOPOLOGY: Linear (ii) MOLECULE TYPE:
        (A) DESCRIPTION: Motif of Synthetase (iii) HYPOTHETICAL: No (iv) ANTI-SENSE: No (vi) ORIGINAL SOURCE:
        (A) ORGANISM: Saccharomyces cerevisiae (vii) IMMEDIATE SOURCE:
        (A) LIBRARY:

(xi) SEQUENCE DESCRIPTION: SEQ ID NO: 14:

Tyr Gly Thr Val Pro His Ser Gly Phe Gly Leu Gly Phe Glu Arg Leu Ile Ala
              5                   10                  15

Tyr Val Thr Gly Val Gln Asn Val Arg Asp Val Ile Pro Phe Pro Arg
        20              25              30

ASSAY FOR DETECTION OF FILARIASIS USING RECOMBINANT ASPARAGINYL-TRNA SYNTHETASE FROM THE HUMAN FILRIAL PARASITE, *BRUGIA MALAYI*

This is a divisional applications Ser. No. 08/628,103 filed Apr. 9, 1996, now U.S. Pat. No. 5,695,962, which is a divisional of Ser. No. 08/441,534, filed May 15, 1995 now U.S. Pat. No. 5,561,154.

GOVERNMENT RIGHTS

This work was performed under National Institutes of Health Grant (NIAID) 08-K1A101019-A-PSA. The U.S. Government has certain rights in this invention.

BACKGROUND OF THE INVENTION (1) Field of the Invention

The present invention relates to a major *Brugia malayi* enzyme which is a biologically active, recombinant asparaginyl-tRNA synthetase. This synthetase functions specifically to aminoacylate tRNA with the amino acid asparagine. Isolation of the filarial enzyme facilitates exploration of structure-function relationships relevant to cognate tRNA binding and biological activity for new drug development against filarial diseases. Further, the synthetase is used in an assay for inhibition or promotion of activity of the enzyme by various compounds. The enzyme is used for producing antibodies used in assays to detect filarial nematodes in biological tissues. The synthetase can also be used to detect antibodies to the synthetase in a biological tissue.

(2) Description of Related Art

Lymphatic filariasis is caused by infection with the filarial nematodes *Brugia malayi, Brugia timori, Wuchereria bancrofti* and *Onchocerca volvulus* which collectively infect about 200 million persons throughout the world. The filarial nematodes cause lymphatic filariasis (elephantiasis) or onchocerciasis (river blindness). New control strategies for these parasites seek to characterize important parasite antigens and biochemical pathways to serve as targets for vaccine or new drug development (Philipp, M., et al., Ann Rev. Microbiol. 42 685–716 (1988)). There is also a need to develop assays for filarial nematodes. The aminoacyl-tRNA synthetases (AARS) are a group of enzymes whose primary function is to specifically attach amino acids to the 3'-adenosine of their cognate tRNAs in a two step process which involves the formation of an enzyme bound aminoacyl-adenylate intermediate (Carter, T. W., Ann. Rev. Biochem. 62 715–748 (1993)). These enzymes thus play a crucial role in ensuring the fidelity of protein biosynthesis by discriminating against incorrect aminoacylation and thus are fundamental to the growth and replication of all forms of life. The structural basis for AARS specificity lies primarily in mechanisms responsible for the recognition of cognate tRNAs. The 20 AARS of both prokaryotes and eukaryotes can now be divided into two classes based on short peptide sequence motifs and catalytic domain topologies: a Rossmann fold for class I and an antiparallel β fold for class II (Eriani, G., et al., Nature 347 203–206 (1990); and Cusack, S., et al., Nature 347 249–255 (1990)).

In the course of immunological studies of filarial parasite antigens, the gene encoding an immunodominant 63 kDa peptide in *B. malayi* was also found within the genome of another major human filarial parasite, *O. volvulus* the organism which causes onchocerciasis (Nilson, T. W., et al., Proc. Natl. Acad. Sci. USA 85 3604–3607 (1988); and Kron, M., et al., Mol. Biochem. Parasit. 52 289–292 (1992)). When originally described, the derived amino acid sequence of the *B. malayi* gene product was thought to have no similarity with previously known proteins. Subsequent to recognition of a second class of AARS in 1990 (Eriani, G., et al., Nature 347 203–206 (1990); and Cusack, S., et al., Nature 347 249–255 (1990)), reanalysis of the *B. malayi* antigen primary structure revealed the presence of one, and possibly two, allowing for the possibility of a frame-shift error in the determination of the gene sequence, structural motifs characteristic of the class II aminoacyl-tRNA synthetases which strongly suggested that the antigen was an asparaginyl-tRNA synthetase (Cusack, S., et al., Nucleic Acids Research 19 3489–3497 1991)). Previously, only a truncated 55 kDa portion of the *B. malayi* peptide had been expressed for immunological studies. There is a need for a pure form of the complete asparaginyl-tRNA synthetase for the reasons discussed above.

OBJECTS

It is therefore an object of the present invention to provide recombinant DNA encoding an asparaginyl-tRNA synthetase of *Brugia malayi*. Further, it is an object of the present invention to provide plasmids and bacteria which contain recombinant DNA and express this synthetase. Further still, it is an object of the present invention to provide an assay method which uses the synthetase as a basis for testing compounds for enhancement or inhibition of the activity of the synthetase. Further still, it is an object of the present invention to use the synthetase to produce an antibody which can be used in an ELISA assay. These and other objects will become increasingly apparent by reference to the following description and the drawings.

BRIEF DESCRIPTION OF THE DRAWINGS

FIG. 1A is a photograph showing an ethidium bromide stained 1% agarose gel of PCR (PCR is polymerase chain reaction) deoxyribonucleic acid products obtained by reverse transcriptase PCR using specific primers. FIG. 1B is a photograph showing a Coomassie Brilliant Blue stained SDS-PAGE gel of purified recombinant asparaginyl-tRNA synthetase (lane 2) indicating a relative molecular weight of about 63 kDa based upon the size standards (lane 1).

FIG. 2 is a graph showing asparagine substrate incorporation into various tRNA's catalyzed by a fusion protein of the synthetase with a maltose binding protein. Open squares are *Escherichia coli* tRNA, solid diamonds are yeast tRNA and solid squares are calf liver tRNA.

FIG. 3 is a chart showing the alignment of three class II aminoacyl-tRNA structural motif sequences with respect to the *B. malayi* and *O. volvulus* antigens and two established asparaginyl-tRNA synthetase.

FIG. 4 is a chart showing the steps of experiments of the present invention.

DESCRIPTION OF PREFERRED EMBODIMENTS

The present invention relates to an isolated and purified protein which comprises recombinant DNA derived asparaginyl-tRNA synthetase of *Brugia malayi*.

Further, the present invention relates to a recombinant DNA encoding an asparaginyl-tRNA synthetase of *Brugia malayi*.

Further, the present invention relates to a recombinant DNA encoding a maltose binding protein and asparaginyl-tRNA synthetase fusion protein, wherein the synthetase is removable by cleaving with Factor Xa.

Further still the present invention relates to an *Escherichia coli* containing recombinant DNA encoding an asparaginyl-tRNA synthetase of *Brugia malayi*.

Further, the present invention relates to an assay method which comprises: providing an isolated and purified protein which comprises a recombinant DNA derived asparaginyl-tRNA synthetase of *Brugia malayi* in an aqueous solution with a compound to be tested for an affect on activity of the synthetase; and determining the effect on activity of the synthetase by the compound.

The present invention also relates to a process for asparaginyl aminoacylation of tRNA which comprises: contacting a mixture of protein comprising a tRNA and asparagine with an isolated and purified recombinant DNA derived aminoacyl-tRNA synthetase of *Brugia Malayi* so as to aminoacylate the tRNA with asparagine.

The present invention relates to an assay for detection of filariasis in an animal which comprises providing a biological sample from the animal suspected of containing filarial nematodes; and detecting aminoacyl-tRNA synthetase in the sample from the nematodes with an antibody to a recombinant DNA derived asparaginyl-tRNA synthetase of *Brugia malayi*. In this assay the synthetase is used to produce a polyclonal or monoclonal antibody in the conventional manner. The antibody can be labeled or used in a sandwich type assay.

Finally the present invention relates to an assay for detection of filariasis in an animal which comprises providing a biological sample from the animal suspected of containing an antibody to filarial nematodes; and binding the antibody with a recombinant DNA derived asparaginyl tRNA synthetase of *Brugia malayi*.

The recombinant DNA is carried in *Escherichia coli* ATCC 69768. This strain was deposited under the Budapest Treaty on Mar. 23, 1995 and is available upon request by strain name and number.

ATCC 69768 includes plasmid pMALCR1 which encodes a maltose binding protein used for isolation of the fusion protein by affinity chromatography and is used extensively by the prior art. This type of fusion protein is described in detail in Current Protocols Supplement 10, 16.6.1 published by New England Biolabs, Beverly, Mass. Factor Xa is used to cleave the maltose binding protein from the protein of interest.

The DNA encoding the synthetase can be incorporated in a non-infective virus, such as a baculovirus and used as a vaccine. A preferred baculovirus host cell SK21 available from Michigan State University, Plant Biology, East Lansing, Mich. 48824.

Confirmation of recombinant asparaginyl-tRNA synthetase activity by the present invention represents the first example of a eukaryotic asparaginyl-tRNA synthetase that has been cloned, expressed and purified, and thus can provide the means by which structure-function relationships of another member of the class II AARS can be studied. The truncated protein described in the prior art was missing a 8 KDa peptide sequence containing the characteristic motif 3 of the class II enzyme in the C-terminal region which is required for active site formation and aminoacylation activity.

The fact that the *Brugia malayi* synthetase was originally identified as strongly immunogenic, is understandable in view of what is known about AARS antigenicity in other species. In the group of human autoimmune diseases known as the idiopathic inflammatory myopathies, antibodies have been identified against several human class II aminoacyl-tRNA synthetases; histidyl-, threonyl-, alanyl- and glycyl-tRNA synthetases (Targoff, I., et al., J. Clin. Invest. 91 2556–64 (1993); and Love, L. A., et al., Medicine 70 360–374 (1991)). Anti-AARS antibodies effectively inhibit enzyme aminoacylation activity in vitro, and are able to immunoprecipitate their respective cognate tRNAs (Bunn, C. C., et al., J. Exp. Med. 163 1281–1291 (1986)). Therefore, it has been hypothesized that tRNA binding sites may be antigenic, representing anti-idiotype epitopes. Because segments of the homodimer interface of the synthetase may function in tRNA, ATP and amino acid binding, identification of important antigenic regions is difficult or unpredictable without the benefit of a biologically active synthetase of the present invention.

The synthetase can be used to locate inhibitors. Such inhibitors are for instance synthetic amino acid adenylates (Biou, V., et al., Science 263 1404–1410 (1994)); and Belrhali, H., et al., Science 263 1432–1436 (1994)). The synthetase can also be used to develop antibodies to the enzyme for use in vitro or in vivo in animals, particularly lower animals and in assays. The synthetase is also useful for asparaginylation of tRNA.

EXAMPLE 1

To explore potential biological activity of the presumed *B. malayi* aminoacyl-tRNA synthetase, a 1615 base pair cDNA encoding the entire filarial antigen peptide was amplified by reverse transcriptase PCR using polyA enriched RNA extracted from adult female *B. malayi* parasites, and this cDNA was subcloned for expression of the corresponding full length peptide. Successful efforts resulted in large scale overproduction and purification of the intact 63 kDa synthetase peptide with only 3 non-parasite residues at the amino terminus of the recombinant protein which are derived from the maltose binding fusion protein utilized to express the gene in *Escherichia coli*.

Figure 1B:
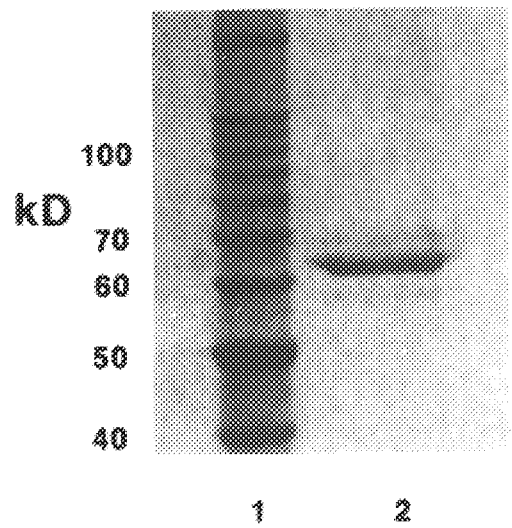

FIG. 1A shows ethidium bromide stained 1% agarose gel demonstrating PCR products obtained by reverse transcriptase PCR using AARS specific oligonucleotide primers. PolyA enriched RNA was extracted from adult female *B. malayi* parasites using standard techniques and 50 nanograms was utilized to synthesize cDNA using reverse transcriptase (TIMESAVER cDNA synthesis, Pharmacia, Inc., Piscataway, N.J.). The resulting cDNA was used as template for amplification of *B. malayi* antigen gene using two gene specific oligonucleotide primers 5': ATGACTGTT-TATATTTGTCCAGAAACTGGAGAT (SEQ ID NO. 1) and 3': TTGAATTCTTATGGGACACATCGACCAA-CAAAGCGAGG (SEQ ID NO. 2), and 30 cycles of amplification using the following thermocycler parameters: hot start at 92° C. for 60 seconds, denaturation; 95° C. for 30 seconds, annealing: 55° C. for 30 seconds, primer extension: 72° C. for 90 seconds, terminal extension: 5 minutes at 72° C. FIG. 1B shows in lane 2 Coomassie Brilliant Blue stained SDS-PAGE gel showing purified recombinant asparaginyl-tRNA synthetase (63kDa). Lane 1 shows the size standard.

EXAMPLE 2

Full length cDNA was subcloned into the plasmid pMAL-cR1 (New England Biolabs, Beverly, Mass.) for large scale overproduction of the recombinant as a fusion protein with the 42 kilodalton maltose binding protein. Growth media in a 20 liter fermenter was seeded with cultures of the *E. coli* Inv α strain harboring a plasmid containing the filarial antigen cDNA, and growth at 30° C. From this culture induced with IPTG (isopropyl-β-D-thiogalacto-pyranoside), 40 grams of bacterial paste was obtained. Milligram quantities of >95% pure recombinant (63kDa) was obtained for aminoacylation activity studies, following a series of chromatographic purification steps which included gel filtration, affinity chromatography (amylose resin), and preparative Factor Xa cleavage of the maltose binding protein fusion product.

EXAMPLE 3

Figure 4:
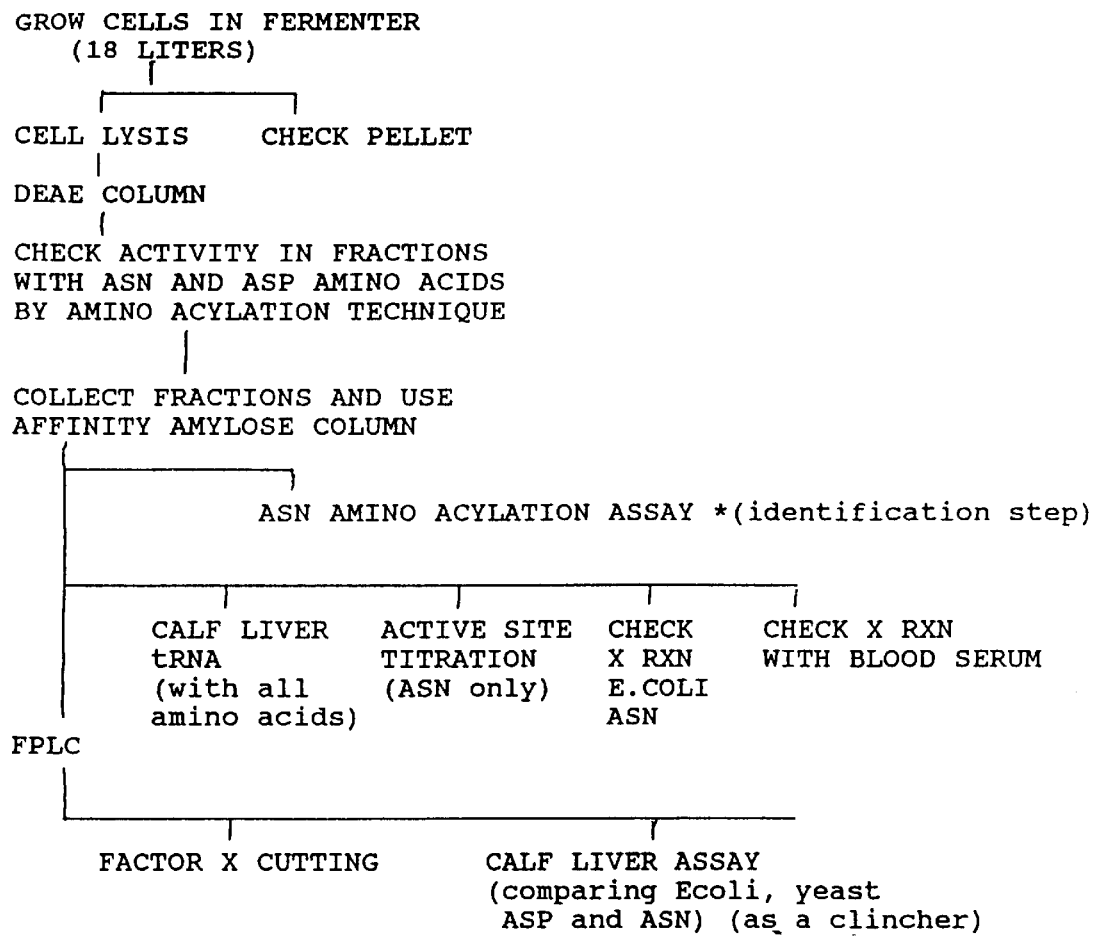

Although the homology analysis of the *B. malayi* antigen amino acid sequence suggested that it might be an asparaginyl-tRNA synthetase, the sequence of the related *O. volvulus* peptide resembled that of an aspartyl-tRNA synthetase (Kron, M., et al., Mol. Biochem. Parasit. 52 289–292 (1992)). To investigate potential amino acid and tRNA specific activities of the recombinant filarial enzyme, aminoacylation studies were conducted using both [$^{4}$C] labelled aspartic acid and asparagine, and unfractionated tRNAs from *E. coli*, yeast and calf liver. With the three tRNAs no amino acid incorporation above control values was observed with [$^{14}$C] aspartic acid. Significant aminoacylation was however found with [$^{14}$C] asparagine, with low incorporation into *E. coli*, intermediate into yeast and high incorporation into calf liver tRNA. Substantial activity is measurable even prior to cleavage of maltose binding protein sequences from the filarial enzyme suggesting that, as in the case of the seryl-tRNA synthetase from *E. coli*, quaternary structure is not perturbed by the additional 42 kDa of the maltose binding protein at the amino terminus nor does this addition significantly hinder conformational changes which might be associated with substrate binding. FIG. 4 shows the steps in this analysis.

Figure 2:
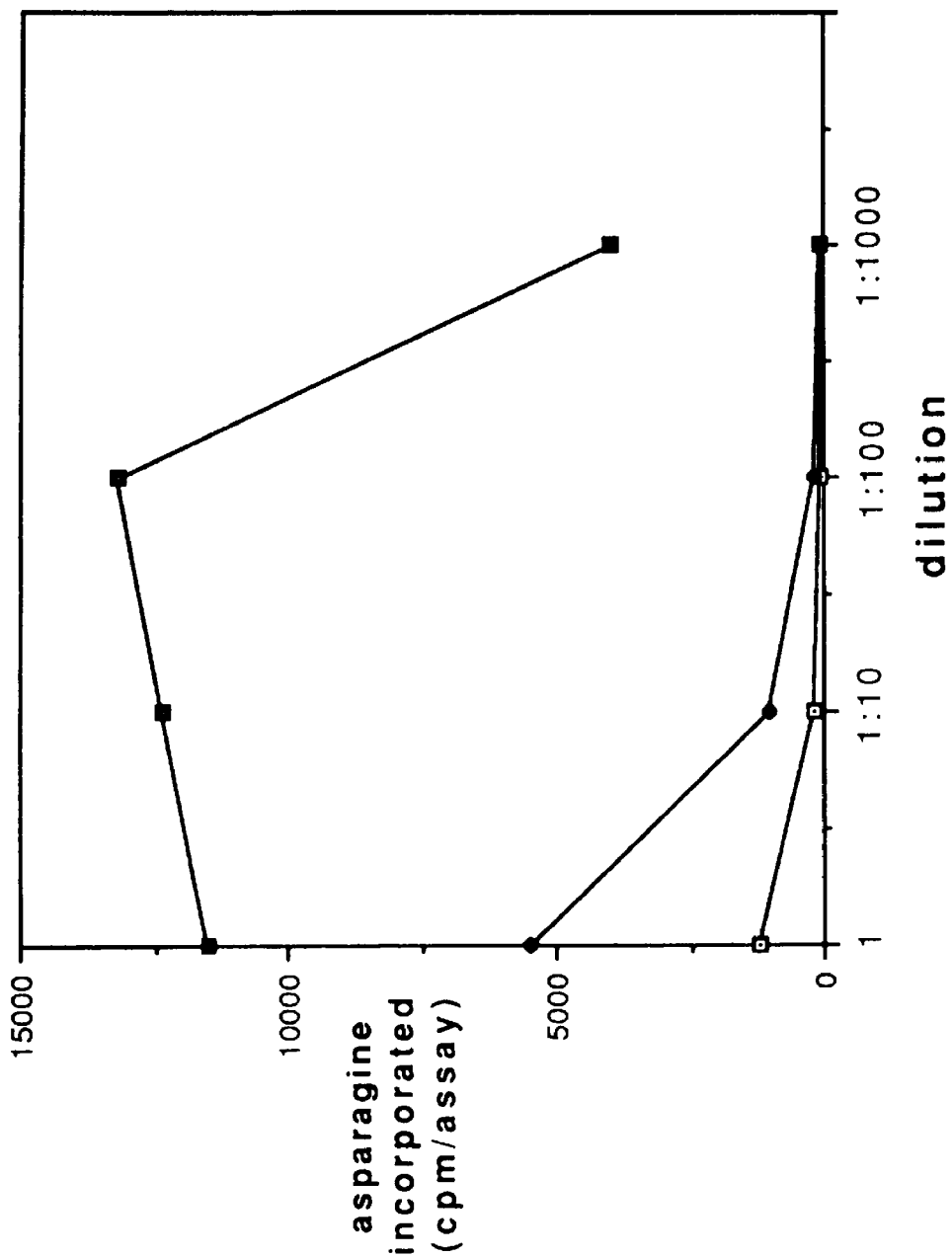

FIG. 2 shows asparagine incorporation into tRNAs catalyzed by the purified 125 kilodalton *B. malayi* antigen fusion protein with maltose binding protein at various dilutions; □ *E. coli* tRNA, ♦ yeast tRNA, ■ calf liver tRNA. Protein sample (10 μl, ca. 3.8 mg/ml undiluted) was added to 40 μl Tris (0.064M) HCl buffer pH 7.6 containing: 0.1 mM L-[$^{14}$c]-asparagine (98 cpm/pmol), 0.5 mM spermidine, 5 mM disodium ATP, 500μg unfractionated *E. coli* or yeast tRNA or 250μg calf liver tRNA. After incubation for 15 min at 37° C., the reaction was quenched with 50 μl of 5% (w/v) TCA (trichloroacetic acid), and the mixture was spotted onto a Whatman GF-A glass fibre filter. The filter was then washed 3 times with 5% TCA, and subsequently with ethanol, ethanol:ether, ether, dried and counted for radioactivity. Parallel measurements made with [$^{14}$C]-aspartic acid showed no incorporation above control values.

FIG. 3 shows alignment of the class II aminoacyl-tRNA synthetase structural motifs (Cusack, S., et al., Nucleic Acids Research 19 265–269 (1991)) sequences of the filarial antigens of *B. malayi* and *O. volvulus*. (antBM and antOV) with those of the asparaginyl-tRNA synthetases from *E. coli* (Anselme, J., et al., Gene 84 481–485 (1989)) (NRSEC) and *Saccharomyces cervesiae* (Bolle, P.-A., et al., Yeast 8 205–213 (1992)). The published DNA sequences for antBM (Nilson, T. W., et al., Proc. Natl. Acad. Sci. USA 85 3604–3607 (1988)) for motif 2 and antOV (Kron, M., et al., Mol. Biochem. Parasit. 52 289–292 (1992)) for motifs 1 and 2 have been corrected for frame shift errors. Residues conserved for the four proteins are in bold type.

The new DNA sequence data for the *B. malayi* asparaginyl-tRNA synthetase (Kron, M., et al., Mol. Biochem. Parasit. 52 289–292 (1992)) demonstrated a discrepancy with the previously published sequence (Nilson, T. W., et al., Proc. Natl. Acad. Sci. USA 85 3604–3607 (1988)), which produced a frameshift that obscured a typical class II aminoacyl-tRNA synthetase motif 2a sequence (RAEK . . . SRTRRH) at amino acids 314–324 (Cusack, S., et al., Nucleic Acids Research 19 265–269 (1991)). Alignment of known asparaginyl tRNA synthetases from *E. coli* and *S. cervesiae* with both the *B. malayi* and *O. volvulus* enzymes now demonstrate typical conservation of active site motifs and tertiary structure as shown in FIG. 3.

Given the high level of expression of message encoding this enzyme in *B. malayi* (Nilson, T. W., et al., Proc. Natl. Acad. Sci. USA 85 3604–3607 (1988)) , it is possible to speculate on the demand for asparaginyl-tRNA synthetase activity in the adult female parasite. Class II AARS in other species also function in the production of adenylated nucleotides, alarmones. The asparaginyl-tRNA synthetase of the present invention can be used for this purpose (EMBL Grenoble Annual Report (1994)). Adenylated nucleotides (e.g. Ap$_4$A) may play a variety of biological roles as signal molecules, regulating both gene expression and enzyme activity (Bochner, B. R., et al. , Cell, 37 225–232 (1984); and Segal, E., et al., Exp. Cell. Res. 167 119–126 (1986)). Since considerable metabolic effort of the adult female parasite is devoted to nutrition and production of viable embryos and larvae, it is conceivable that the high level of asparaginyl-tRNA synthetase expression reflects unusual metabolic demands associated with larval maturation and thus is a target for inhibition.

Ten years ago, the observation that filarial protein synthesis was highly sensitive and specific for certain new experimental antihelminthics, lead to the belief that aminoacyl-tRNA synthetases would indeed be excellent targets for the development of new targeted drug design (Walter, R. D., Trop. Med. Parasitol. 37 95 (1986)). Studies of the crystal structure of a seryl-tRNA synthetase from *E. coli* complexed with cognate tRNA and two synthetic seryl adenylate intermediates (Biou, V., et al., Science 263 1404–1410 (1994)); and Belrhali, H., et al., Science 263 1432–1436 (1994)) confirm that inhibition of AARS catalytic sites is possible. tRNA binding domains of the AARS distant from the catalytic site are probably the best targets for specific and low toxicity enzyme inhibition, since such domains are likely to be structurally different in the parasite and its host due to differences in the evolution of their tRNA substrates.

The amino acid sequence of the t-RNA synthetase of the present invention can be used to prepare a DNA probe for isolation of other synthetases. This can be done by making a DNA probe and using PCR to isolate the DNA encoding the other synthetases. The DNA probe can be used to screen a library directly and in the PCR reactions.

The foregoing description is only illustrative of the present invention and the present invention is limited only by the hereinafter appended claims.

We claim:

1. An assay for detection of filariasis in an animal which comprises:

(a) providing a biological sample from the animal suspected of containing filarial nematodes expressing asparaginyl-tRNA synthetase;

(b) contacting the biological sample with an antibody to a recombinant DNA derived full length purified and enzymatically active asparaginyl-tRNA synthetase of *Brugia malayi* so that the antibody binds to the asparaginyl-tRNA synthetase in the sample;

(c) detecting asparaginyl-tRNA synthetase in the sample bound to the antibody; and (d) correlating the antibody bound to the asparaginyl t-RNA synthetase to the filariasis.

2. The assay of claim 1 wherein the antibody is produced using the asparaginyl-tRNA synthetase derived from *Escherichia coli* ATCC 69768.

* * * * *